(12) United States Patent
Samain et al.

(10) Patent No.: US 7,201,779 B2
(45) Date of Patent: *Apr. 10, 2007

(54) DYE COMPOSITION COMPRISING AT LEAST ONE DIRECT DYE CONTAINING MIXED CHROMOPHORES

(75) Inventors: Henri Samain, Bievres (FR); Grégory Plos, Tokyo (JP); Leila Hercouet, Chelles (FR); Andrew Greaves, Montevrain (FR)

(73) Assignee: L'Oreal S.A. (FR)

( * ) Notice: Subject to any disclaimer, the term of this patent is extended or adjusted under 35 U.S.C. 154(b) by 302 days.

This patent is subject to a terminal disclaimer.

(21) Appl. No.: 10/980,900

(22) Filed: Jun. 16, 2004

(65) Prior Publication Data

US 2005/0204483 A1 Sep. 22, 2005

Related U.S. Application Data

(60) Provisional application No. 60/499,337, filed on Sep. 3, 2003.

(30) Foreign Application Priority Data

Jun. 16, 2003 (FR) .................................. 03 07185

(51) Int. Cl.
*A61K 7/13* (2006.01)

(52) U.S. Cl. ........................ 8/405; 8/406; 8/407; 8/410; 8/411; 8/423; 8/426; 8/437; 8/565; 8/566; 8/567; 8/568; 8/570; 8/573; 8/574; 8/608; 534/269.4; 548/301.7

(58) Field of Classification Search .................... 8/405, 8/406, 407, 410, 411, 423, 426, 437, 565, 8/566, 567, 568, 570, 573, 574, 608; 534/269.4; 548/301.7

See application file for complete search history.

(56) References Cited

U.S. PATENT DOCUMENTS

| | | | |
|---|---|---|---|
| 3,100,739 A | 8/1963 | Kaiser et al. | |
| 3,524,842 A | 8/1970 | Grossman et al. | |
| 3,578,386 A | 5/1971 | Kalopissis et al. | |
| 3,617,163 A | 11/1971 | Kalopissis et al. | |
| 3,817,698 A | 6/1974 | Kalopissis et al. | |
| 3,867,456 A | 2/1975 | Kalopisis et al. | |
| 3,955,918 A | 5/1976 | Lang | |
| 4,025,301 A | 5/1977 | Lang | |
| 4,226,784 A | 10/1980 | Kalopissis et al. | |
| 4,823,985 A | 4/1989 | Grollier et al. | |
| 4,886,517 A | 12/1989 | Bugaut et al. | |
| 5,708,151 A * | 1/1998 | Mockli | 534/608 |
| 5,879,413 A | 3/1999 | Pengilly et al. | |
| 5,888,252 A | 3/1999 | Mockli | |
| 5,919,273 A | 7/1999 | Rondeau et al. | |
| 5,980,587 A | 11/1999 | Samain | |
| 5,993,490 A | 11/1999 | Rondeau et al. | |
| 6,045,591 A | 4/2000 | Deneulenaere | |
| 6,136,042 A | 10/2000 | Maubru | |
| 6,179,881 B1 | 1/2001 | Henrion et al. | |
| 6,297,362 B1 | 10/2001 | Kunde et al. | |
| 6,368,360 B2 | 4/2002 | Samain | |
| 6,416,770 B1 | 7/2002 | Leduc et al. | |
| 6,458,167 B1 | 10/2002 | Genet et al. | |
| 6,530,959 B1 | 3/2003 | Lang et al. | |
| 6,797,013 B1 | 9/2004 | Cotteret et al. | |
| 6,863,883 B1 | 3/2005 | Tsujino et al. | |
| 6,884,265 B2 | 4/2005 | Vidal et al. | |
| 2001/0001333 A1 | 5/2001 | Samain | |
| 2001/0044975 A1 | 11/2001 | Matsunaga et al. | |
| 2003/0066143 A1 | 4/2003 | Mockli | |
| 2005/0039268 A1 | 2/2005 | Plos et al. | |

FOREIGN PATENT DOCUMENTS

| | | |
|---|---|---|
| DE | 25 27 638 | 5/1976 |
| DE | 25 38 363 | 5/1976 |
| DE | 33 35 956 | 4/1985 |
| DE | 41 37 005 | 5/1993 |
| DE | 42 20 388 | 12/1993 |
| DE | 198 45 640 | 4/2000 |
| EP | 0 318 294 | 5/1989 |
| EP | 0 714 954 | 6/1996 |
| EP | 0 810 851 | 12/1997 |
| EP | 0 850 636 | 7/1998 |
| EP | 0 850 637 | 7/1998 |
| EP | 0 860 636 | 8/1998 |
| EP | 0 918 053 | 5/1999 |

(Continued)

OTHER PUBLICATIONS

Co-pending U.S. Appl. No. 10/980,899 to Henri Samain et al., filed Jun. 16, 2004.

(Continued)

Primary Examiner—Eisa Elhilo
(74) Attorney, Agent, or Firm—Finnegan, Henderson, Farabow, Garrett & Dunner LLP

(57) ABSTRACT

The invention relates to a dye composition comprising a direct dye consisting of different chromophores, the dye having a particular $L^*a^*b^*$ value.

The invention also relates to the dyeing process using this composition and to the use of this composition for dyeing keratin fibers.

These compositions in particular make it possible to obtain particularly fast colorations.

44 Claims, No Drawings

FOREIGN PATENT DOCUMENTS

| | | |
|---|---|---|
| EP | 0 920 856 | 6/1999 |
| EP | 1 062 940 | 12/2000 |
| EP | 1 133 975 | 9/2001 |
| EP | 1 133 976 | 9/2001 |
| FR | 1 221 122 | 5/1960 |
| FR | 1 516 943 | 3/1968 |
| FR | 1 540 423 | 9/1968 |
| FR | 1 560 664 | 3/1969 |
| FR | 1 567 219 | 5/1969 |
| FR | 2 189 006 | 1/1974 |
| FR | 2 275 462 | 1/1976 |
| FR | 2 285 851 | 4/1976 |
| FR | 2 570 946 | 4/1986 |
| FR | 2 586 913 | 3/1987 |
| FR | 2 757 385 | 6/1998 |
| FR | 2 788 433 | 7/2000 |
| FR | 2 825 625 | 12/2002 |
| GB | 0 738 585 | 10/1955 |
| GB | 1 163 385 | 9/1969 |
| GB | 1 195 386 | 6/1970 |
| GB | 1 491 930 | 11/1977 |
| GB | 1 514 466 | 6/1978 |
| WO | WO 95/01772 | 1/1995 |
| WO | WO 95/15144 | 6/1995 |
| WO | WO 97/44004 | 11/1997 |
| WO | WO 99/48465 | 9/1999 |
| WO | WO 01/66646 | 9/2001 |
| WO | WO 02/30374 | 4/2002 |
| WO | WO 02/078596 | 10/2002 |
| WO | WO 03/006554 | 1/2003 |
| WO | WO 03/018021 | 3/2003 |
| WO | WO 03/029359 | 4/2003 |
| WO | WO 03/030909 | 4/2003 |

OTHER PUBLICATIONS

French Search Report for French Application No. 03 07185 (Priority Application for U.S. Appl. No. 10/980,900) dated Mar. 15, 2004, Examiner Irwin.

French Search Report for French Application No. 03 07186 (Priority Application for U.S. Appl. No. 10/980,899) dated Mar. 11, 2004, Examiner Vayssié.

Seidler et al., "The qualification of different ditetrazolium salts as indicators in the oxido-reductase historchemistry," Acta Histochem. vol. 61(1), pp. 48-52 (1978).

Alberti et al., "Cationic Dyes for Acrylic Fibres v. Cationic Dyes Derived From Several Heterocyclic Amines With Two or more Heteroatoms," Ann. Chim (Rome) vol. 65(Nos. 5-6), pp. 305-314 (1975).

Alberti et al., "Ricerche Sui Coloranti Cationic Per Fibra Acrylica," Chim. Ind. (Milan) vol. 56(No. 9), pp. 600-603 (1974).

Savarino et al., "Disperse and Cationic Dyes from Aminophenyl-X-Azolo-Pyridines," Dyes Pigm., vol. 11(No. 3), pp. 163-172 (1989).

Viscardi et al., "Disperse and Cationic Azo Dyes from Heterocyclic Intermediates," Dyes Pigm., vol. 19(No. 1) pp. 69-79 (1992).

Neidlin et al., "Synthese von substituierten Pyridiniumsalzen," Ger. Monatsh. Chem., vol. 106(No. 3), 643-648 (1975).

Tien et al., "Syntheses of New Azo Dyestuff Containing a Sydnone Ring," Journal of the Chinese Chemical Society (Taipei), vol. 45(No. 1), pp. 209-211 (1998).

Khim Tekhnol., vol. 22(No. 5) pp. 548-553 (1979).

Holla et al., "Studies on Nitrofuran Heterocycles, Part I," Rev. Roum. Chim., vol. 33(No. 4), pp. 277-282 (1998).

Alberti et al., "Thermodynamic Features in Acrylic Fiber Dyeing with Basic Dyes," Text. Res. J., vol. 54(No. 2), pp. 105-107 (1984).

Kuznetsova et al., "The determination of Thickness of a Histological Section by Interference Microscopy," Tsitologiya, vol. 10(No. 3), pp. 403-405 (1968), Abstract.

Zh. Obshch. Khim., vol. 40(No. 1), pp. 195-202 (1970).

The Journal of General Chemistry of the USSR (translated from Russian), vol. 40(1), pp. 178-183. (English translation of Zh. Obshch. Khim., vol. 40(No. 1), pp. 195-202) (1970).

Whittemore et al., "Subtype-Selective N-Methyl-D-aspartate Receptor Antagonists: Benzimidazalone and Hydantoin as Phenol Replacements," Journal of Medicinal Chemistry, vol. 43(No. 9), pp. 1892-1897 (2000).

K. Venkateraman, *The Chemistry of Synthetic Dye*, vol. 1 to 7 Academic Press (1952).

"Dyes and Dye Intermediate," *Kirk Othmer Encyclopedia of Chemical Technology*, 7th ed.; Wiley and Sons (1993).

"The Design and Synthesis of Bisazo Series Compound Used in Organophotconductor," MRL Bull. Res. Dev. vol. 6, No. 2, pp. 21-27 (1992).

Lihua Jianyan, Huaxue Fence, vol. 29, No. 4, pp. 233-234 (1993).

"2,4,6-Gemischtfunktionell substituierte 1,3,5-Triazine," Chemikur Zeitung, vol. 111 No. 7/8, pp. 241-245 (1987).

English Language Derwent Abstract to DE 33 35 956.

English Language Derwent Abstract to DE 41 37 005.

English Language Derwent Abstract to DE 42 20 388.

\* cited by examiner

DYE COMPOSITION COMPRISING AT LEAST ONE DIRECT DYE CONTAINING MIXED CHROMOPHORES This application claims benefit of U.S. Provisional Application No. 60/499,337, filed Sep. 3, 2003, the contents of which are incorporated herein by reference. This application also claims benefit of priority under 35 U.S.C. § 119 to French Patent Application No. 03 07185, filed Jun. 16, 2003, the contents of which are also incorporated herein by reference.

The invention relates to a dye composition comprising a direct dye consisting of different chromophores. The invention also relates to the dyeing process using this composition, and to the use of this composition for dyeing keratin fibers.

It is known practice to dye keratin fibers, and in particular human hair, with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds, which, when combined with oxidizing products, may give rise to colored compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colors to be obtained.

This oxidation dyeing process consists in applying to keratin fibers bases or a mixture of bases and of couplers with aqueous hydrogen peroxide solution as oxidizing agent, leaving the mixture to act on the fibers, and then rinsing the fibers. The colorations resulting therefrom are permanent, strong and resistant to external agents, especially to light, bad weather, washing, perspiration and rubbing. This process, which is generally performed at basic pH, makes it possible to obtain dyeing and simultaneous lightening of the fiber, which is reflected in practice by the possibility of obtaining a final coloration that is lighter than the original color. In addition, lightening of the fiber has the advantageous effect of creating a unified color in the case of gray hair, and of bringing out the color, i.e. of making it more possible, in the case of naturally pigmented hair.

It is also known practice to dye keratin fibers by direct dyeing. This process conventionally used in direct dyeing consists in applying to the keratin fibers direct dyes, which are colored and coloring molecules that have affinity for the fibers, leaving the dyes to act on the fibers, and then rinsing the fibers.

It is known practice, for example, to use direct dyes of the nitrobenzene type, anthraquinone dyes, nitropyridines, or dyes of the azo, xanthene, acridine, azine or triarylmethane type.

Certain direct dyes may be combined with oxidizing agents, thus making it possible to obtain lightening of the fiber at the time of dyeing. For example, patent application EP 810 851 describes dye compositions containing direct dyes comprising at least one quaternized nitrogen atom of the azo or azomethine type, which may be mixed extemporaneously at basic pH with an oxidizing composition.

The colorations resulting from the use of direct dyes are temporary or semi-permanent colorations, since the nature of the interactions that bind the direct dyes to the keratin fiber, and their desorption from the surface and/or the core of the fiber, are responsible for their poor dyeing power and their poor wash-fastness and perspiration-fastness.

These direct dyes may consist of one or more chromophores, which may be identical or different. Dyes consisting of several chromophores are described, for example, in documents FR 1 540 423, EP 1 133 975, EP 1 133 976, U.S. Pat. No. 5,708,151 and WO 02/078596. All these dyes make it possible to obtain chromatic colors, i.e. glint-rich colors such as bright oranges, bright yellows, bright reds, etc.

To obtain a non-chromatic coloration, direct dyes are used as a mixture. In particular, to obtain fundamental colors, i.e. colors ranging from black to natural blond, passing through browns, dye compositions generally comprising a mixture of blue or violet direct dyes and of yellow or orange direct dyes are used. The problem encountered with these mixtures is that the various dyes do not have the same affinity for the hair or the same resistance to external agents, which results over time in impairment of the initial color. For example, after shampooing several times, a change in the coloration toward violet or yellow may be observed, as a function of the affinity of each of the dyes for the keratin fiber.

The aim of the present invention is to provide direct dyes that can overcome the drawbacks of the existing direct dyes. In particular, one of the aims of the present invention is to provide direct dyes that allow fundamental shades to be obtained without the problem of the color changing over time. Another aim of the invention is to provide direct dyes which allow keratin fibers to be dyed as strongly as with oxidation dyes, which are as stable as said oxidation dyes to light, resistant to bad weather, washing and perspiration, and also sufficiently stable in the presence of oxidizing and reducing agents to be able simultaneously to obtain lightening of the fiber.

This aim is achieved with the present invention, one aim of which is a dye composition comprising, in a suitable dyeing medium, a mixed dye consisting of several chromophores linked together via a linker, at least two of these chromophores being different, the chromophores being chosen such that the mixed dye, in a composition containing $4.7 \times 10^{-4}$ mol of dye for 100 g of composition, gives, in a standardized coloration test on a lock of hair containing 90% white hairs, the following values in the L*a*b* calorimetric system:

if $a^* \geq 0$ and $b^* \geq 0$,
   then a* belongs to the range [0; +20] and b* belongs to the range [0; +40]
if $a^* \leq 0$ and $b^* \geq 0$,
   then a* belongs to the range [−27; 0] and b* belongs to the range [0; +40]
if $a^* \geq 0$ and $b^* \leq 0$,
   then a* belongs to the range [0; +9] and b* belongs to the range [−10; 0]
if $a^* \leq 0$ and $b^* \leq 0$,
   then a* belongs to the range [−14; 0] and b* belongs to the range [−21; 0].

A subject of the invention is also a dyeing process using this composition.

Another subject of the invention is the use of the composition of the present invention for dyeing keratin fibers, in particular human keratin fibers such as the hair, in particular to obtain good shampoo resistance.

Finally, a subject of the invention is mixed dyes as defined above.

Specifically, the composition of the present invention makes it possible to obtain a coloration of keratin fibers in fundamental shades ranging from black to natural blond, which is fast with respect to various external agents, in particular shampoo. The composition furthermore makes it possible to avoid the problems of changing of the color over time.

The measurement of the L*a*b* values as defined in the present invention must be performed using a reference composition containing:

| | |
|---|---|
| Mixed dye useful for the invention | $4.7 \times 10^{-4}$ mol |
| Alkyl (C8/C10 50/50) polyglucoside (2) as a buffered aqueous 60% solution sold under the name Oramix-CG110 by the company SEPPIC | 10 g |
| Benzyl alcohol | 10 g |
| Polyethylene glycol 400 containing 8 ethylene oxide units | 12 g |
| 20.5% aqueous ammonia | 13 g |
| Demineralized water | qs 100 g |

The reference composition is applied at room temperature to locks of natural hair containing 90% white hairs (T=23° C.±3° C.). After a leave-on time of 20 minutes, the locks are rinsed and dried. The L*a*b* values are measured using a CM 2002 colorimeter, illuminant D65-10° SCI.

In the L*a*b* system, the three parameters denote, respectively, the luminance (L*), the hue (a*) and the saturation (b*). According to this system, the higher the value of L*, the paler or less luminant the color. Conversely, the smaller the value of L*, the darker or more luminant the color a* and b* indicate two color axes, a* indicating the green/red color axis and b* the blue/yellow color axis.

According to one preferred embodiment, the L*a*b* values of the mixed dye that is useful in the present invention are such that:
if $a^* \geq 0$ and $b^* \geq 0$,
  then a* belongs to the range [0; +15] and b* belongs to the range [0; +30]
if $a^* \leq 0$ and $b^* \geq 0$,
  then a* belongs to the range [−20; 0] and b* belongs to the range [0; +30]
if $a^* \geq 0$ and $b^* \leq 0$,
  then a* belongs to the range [0; +6] and b* belongs to the range [−6; 0]
if $a^* \leq 0$ and $b^* \leq 0$,
  then a* belongs to the range [−10; 0] and b* belongs to the range [−15; 0].

Preferably, the chromaticity C* calculated according to the formula below is less than 20.

$$C^* = \sqrt{(a^*)^2 + (b^*)^2}.$$

According to the present invention, the term "chromophore" means a radical derived from a dye, i.e. a radical derived from a molecule that absorbs in the visible radiation range (between 400 and 800 nm).

For the purposes of the present invention, the chromophores are said to be different when they differ in their chemical structure. Such chromophores may be chromophores derived from different families or from the same family, on condition that they have different chemical structures. For example, the chromophores may be chosen from the family of azo dyes, but differ in the chemical structure of the radicals of which they are composed.

As chromophores that are useful in the present invention, mention may be made of radicals derived from the following dyes: acridines, acridones, anthranthrones, anthrapyrimidines, anthraquinones, azines, azos, azomethines, benzanthrones, benzimidazoles, benzimidazolones, benzindoles, benzoxazoles, benzopyrans, benzothiazoles, benzoquinones, bis-azines, bis-isoindolines, carboxanilides, coumarins, cyanins (azacarbocyanin, diazacarbocyanin, diazahemicyanin, hemicyanin and tetraazacarbocyanin), diazines, diketopyrrolopyrroles, dioxazines, diphenylamines, diphenylmetharies, dithiazines, flavonoids such as flavanthrones and flavones, fluorindines, formazans, hydrazones, in particular arylhydrazones, hydroxy ketones, indamines, indanthrones, indigoids and pseudo-indigoids, indophenols, indoanilines, isoindolines, isoindolines, isoindolinones, isoviolanthrones, lactones, methines, naphthalimides, naphthanilides, naphtholactams, naphthoquinones, nitro dyes, especially nitro (hetero)aromatic dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, xanthenes.

As chromophores that are useful in the present invention, mention may be made even more particularly of radicals derived from the following dyes: acridines, acridones, anthranthrones, anthraquinones, azines, azos, azomethines, benzanthrones, benzoquinones, bis-azines, cyanins (azacarbocyanin, diazacarbocyanin, diazahemicyanin, hemicyanin and tetraazacarbocyanin), diazines, diketopyrrolopyrroles, dioxazines, diphenylmethanes, dithiazines, flavonoids such as flavanthrones and flavones, formazans, hydrazones, in particular arylhydrazones, indamines, indanthrones, indigoids and pseudo-indigoids, indophenols, indoanilines, isoviolanthrones, methines, naphthalimides, naphtholactams, naphthoquinones, nitro dyes, especially nitro(hetero)aromatic dyes, phenazines, phenothiazines, phthalocyanin, polyenes/carotenoids, porphyrins, pyrazolone, quinacridones, quinophthalones, tetrazoliums, thiazines, thioindigo, thiopyronines, triarylmethanes, xanthenes.

Among the nitro chromophores that may be used according to the invention, mention may be made in a non-limiting manner of the radicals derived from the following compounds:
1,4-diamino-2-nitrobenzene
1-amino-2-nitro-4-(β-hydroxyethyl)aminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis-(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-[tris(hydroxymethyl)methylamino]-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene 1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo chromophores that may be used according to the invention, mention may be made of the radicals derived from the cationic azo dyes described in patent applications WO 95/15144, WO-95/01772 and EP-714 954.

Among the azo chromophores that may also be mentioned are the following compounds, described in the Color Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalene-sulfonic acid.

Among the quinone chromophores that may be mentioned are the radicals derived from the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine chromophores that may be mentioned are the radicals derived from the following dyes:
Basic Blue 17
Basic Red 2.

Among the triarylmethane chromophores that may be used according to the invention, mention may be made of the radicals derived from the following dyes:
Basic Green 1
Acid Blue 9
Basic Violet 3
Basic Violet 14
Basic Blue 7
Acid Violet 49
Basic Blue 26
Acid Blue 7.

Among the indoamine chromophores that may be used according to the invention, mention may be made of the radicals derived from the following dyes:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

Mention may also be made of the chromophores described in documents U.S. Pat. No. 5,888,252, EP 1 133 975, WO 03/029359, EP 860 636, WO 95/01772, WO 95/15144 and EP 714 954. Mention may also be made of those mentioned in the encyclopedia "The chemistry of synthetic dye" by K. Venkataraman, 1952, Academic Press, vol. 1 to 7, in encyclopedia "Kirk-Othmer" "Chemical Technology", in the chapter "Dyes and Dye Intermediate", 1993, Wiley & Sons, and in various chapters of the encyclopedia "Ullmann's Encyclopedia of Industrial Chemistry" 7th edition, Wiley & Sons.

Preferably, the chromophores are chosen from azo, xanthene, hydrazone and especially arylhydrazone, phenothiazine, acridine, cyanin, for instance tetraazacarbocyanin, anthraquinone, methine, azomethine, diketopyrrolopyrrole, indigoid and nitro, especially nitro(hetero)aromatic, chromophores.

According to one even more particular embodiment, the chromophores are chosen from azo, hydrazone, especially arylhydrazone, cyanin, for instance tetraazacarbocyanin, anthraquinone, methine, azomethine and nitro, especially nitro(hetero)aromatic, chromophores.

According to a first particular embodiment, the mixed dye comprises at least one chromophore which, by itself, has a positive or zero value of a* and b*, and at least one chromophore which, by itself, has a negative value of a* and b*.

According to a second particular embodiment, the mixed dye comprises at least one chromophore which, by itself, has a positive or zero value of a* and a negative or zero value of b*, and at least one chromophore which, by itself, has a negative value of a* and a positive value of b*.

According to a third particular embodiment, the mixed dye comprises at least one chromophore which, by itself, has a positive or zero value of a* and b* and at least one chromophore which has a positive or zero value of a* and a negative value of b*.

According to a fourth particular embodiment, the mixed dye comprises at least one chromophore which, by itself, has a positive or zero value of a* and b* and at least one chromophore which, by itself, has a negative value of a* and a positive value of b*.

According to a fifth particular embodiment, the mixed dye comprises at least one chromophore which, by itself, has a positive or zero value of a* and a negative or zero value of b*, and at least one chromophore which, by itself, has a negative value of a* and b*.

According to a sixth particular embodiment, the mixed dye comprises at least one chromophore which, by itself, has a negative or zero value of a* and b* and at least one chromophore which, by itself, has a negative value of a* and a positive value of b*.

According to the present invention, the mixed dye preferably comprises two to four different chromophores, and preferably two or three different chromophores.

Preferably, the mixed dye of the invention corresponds to the formula

Dye-1-L-Dye-2 in which L is a cationic or non-cationic linker, and Dye 1 and Dye 2 are different chromophores.

According to one particular embodiment of the invention, the mixed dye is a cationic dye. In the context of the invention, the term "cationic mixed dye" means a dye whose cationic charge may form an integral part of the chromophore and/or of the linker, or alternatively a dye whose cationic charge is present via a substituent of the chromophore and/or of the linker.

According to one particular embodiment, the mixed dye comprises at least one cationic chromophore and preferably at least two cationic chromophores, the cationic charge forming an integral part of the chromophore or being borne by a substituent, the linker possibly being cationic.

According to another particular embodiment, the mixed dye is at least di-cationic, the cationic fillers being borne by the chromophores and/or by the linker. According to a variant of this embodiment, at least two of the chromophores are cationic chromophores, the linker possibly being cationic.

The cationic chromophore(s) is (are) generally chromophores comprising a quaternized nitrogen atom, directly or as substituent.

These cationic chromophores are, for example, chromophores comprising, directly or as substituent, an alkylammonium, imidazolium, pyridinium, quinolinium, acridinium, benzimidazolium, benzobistriazolium, benzopyrazolium (or indazolium), benzopyridazinium, benzoquinolium, benzothiazolium, benzotriazolium, benzoxazolium, bi-pyridinium, bis-tetrazolium, dihydrothiazolium, imidazopyridinium, indolium, isoquinotinium, naphthimidazolium, naphthoxazolium, naphthopyrazolium, oxadiazolium, oxazolium, oxazolopyridinium, phenazinium, phenoxazolium, pyrazinium, pyrazolium, pyrazoyltriazolium, pyridinoimidazolium, quinolium, tetrazolium, thiadiazolium, thiazolium, thiazolopyridinium, thiazoylimidazolium, thiopyrylium, triazolium or xanthylium radical.

Preferably, these chromophores comprise, directly or as substituent, an alkylammonium, imidazolium, pyridinium, acridinium, benzimidazolium, benzopyrazolium (or indazolium), benzopyridazinium, bi-pyridinium, bis-tetrazolium, imidazopyridinium, indolium, naphthimidazolium, naphthopyrazolium, phenazinium, pyrazinium, pyrazolium, pyridinoimidazolium or xanthylium radical.

Examples of cationic chromophores that are useful in the present invention have been mentioned previously. Other examples are given in patent applications WO 95/01772, WO 95/15144, EP 714 954, EP 318 294 and WO 03/029359.

According to one variant, the mixed dye comprises cationic azo chromophores. Such chromophores are described, for example, in EP 0 850 636, FR 2 788 433, EP 920 856, WO 99/48465, FR 2 757 385, EP-850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 95/15144, GB 1 195 386, U.S. Pat. No. 3,524,842, U.S. Pat. No. 5,879,413, EP 1 062 940, EP 1 133 976, GB 738 585, DE 2 527 638, FR 2 275 462, GB 1974-27645, Acta Histochem. (1978), 61(1), 48–52, Tsitologiya (1968), 10(3), 403–5, Zh. Obshch. Khim. (1970), 40(1), 195–202, Ann. Chim. (Rome) (1975), 65(5–6), 305–14, Journal of the Chinese Chemical Society (Taipei) (1998), 45(1), 209–211, Rev. Roum. Chim. (1988), 33(4), 377–83, Text. Res. J. (1984), 54(2), 105–7, Chim. Ind. (Milan) (1974), 56(9), 600–3, Khim. Tekhnol. (1979), 22(5), 548–53, Ger. Monatsh. Chem. (1975), 106(3), 643–8, MRL Bull. Res. Dev. (1992), 6(2), 21–7, Lihua Jianyan, Huaxue Fence (1993), 29(4), 233–4, Ann. Chim. (Rome) (1975), 65(5–6), 305–14, Dyes Pigm. (1992), 19(1), 69–79, Dyes Pigm. (1989), 11(3), 163–72.

In the context of the present invention, the term "linker" means an atom or a group of atoms separating the chromophores from the mixed dye. The atoms of the linker must be such that the position on the scale of wavelengths of the absorption maxima(s) of the chromophores constituting the mixed dye should not be modified by more than 30 nanometers relative to the absorption maxima of each of the chromophores taken separately, i.e. not linked together via the linker, more particularly not more than 15 nm and preferably not more than 10 nm. The linker may be cationic or non-cationic.

According to one variant, the linker is an atom or a group of atoms that isolates each of the chromophores so as to stop electronic delocalization of each of the chromophores.

The linker is, for example, a $C_1$–$C_{20}$, preferably $C_1$–$C_{14}$ and even more particularly $C_1$–$C_6$, linear, branched or cyclic, optionally substituted hydrocarbon-based chain, one or more of the carbon atoms of the chain possibly being replaced with at least one hetero atom such as sulfur, nitrogen or oxygen, and/or with at least one group comprising a hetero atom, such as a carbonyl group, the hydrocarbon-based chain possibly being unsaturated or containing at least one optionally substituted alkylene radical; an optionally substituted arylene radical; an optionally substituted divalent terephthalamide radical; an optionally substituted divalent heterocyclic radical, for instance a divalent triazine radical, or an —NH—CO— radical.

The hydrocarbon-based chain, but also the alkyl(en)e radicals, may be substituted, for example, with at least one hydroxyl radical, an alkoxy radical, especially of C1–C6, a C1–C6 (poly)hydroxyalkoxy group, an amino group, an alkylamino group comprising one or more identical or different C1–C6 alkyl radicals optionally bearing at least one hydroxyl group, at least one halogen, etc.

Examples of linkers that may be mentioned include alkylene radicals ($C_nH_2n$) more especially containing 1 to 14 carbon atoms and preferably 1 to 6 carbon atoms, for example methylene, ethylene, propylene, etc., optionally substituted as indicated above, optionally interrupted with at least one hetero atom such as sulfur, nitrogen or oxygen, and/or a group comprising a hetero atom such as a carbonyl group; optionally substituted (hetero)arylene radicals, for example phenylene or naphthylene, phenanthrylene, triazinyl, pyrimidinyl, pyridyl, pyridazinyl, or quinoxalinyl, which are optionally substituted; Alkyl-aryl-Alkyl radicals or Alkyl-heteroaryl-Alkyl radicals, the alkyl portions of the radicals more particularly comprising from 1 to 6 carbon atoms.

The (hetero)arylene radicals mentioned above may be substituted with one or more of the following radicals: C1–C6 alkyl; C1–C6 alkoxy; C2–C6 (poly)hydroxyalkoxy; amino; amino substituted with one or more identical or different C1–C6 alkyl radicals optionally bearing at least one hydroxyl group and/or substituted with a C6 aryl radical optionally substituted with one or more C1–C6 alkyl, C1–C6 alkoxy, C2–C6 (poly)hydroxyalkoxy or amino groups, or amino groups substituted with one or more identical or different C1–C6 alkyl radicals optionally bearing at least one hydroxyl group; trifluoromethyl; cyano; alkylamido, especially of C1–C6; RCOO— with R representing a C1–C6 alkyl radical.

More particular examples that may be mentioned include:

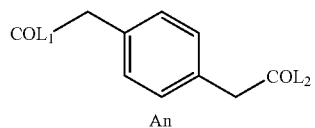

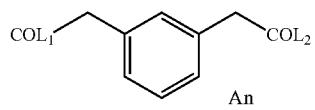

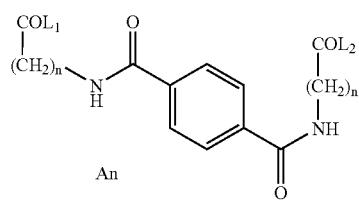

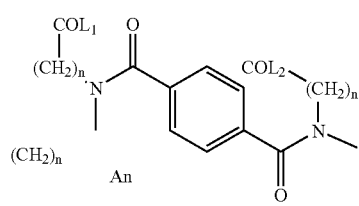

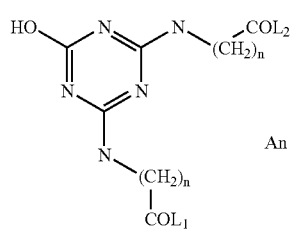

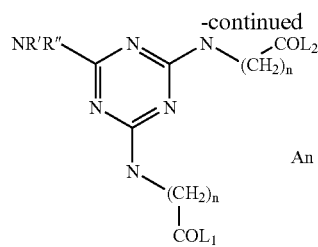

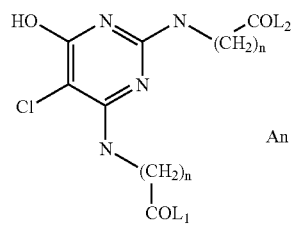

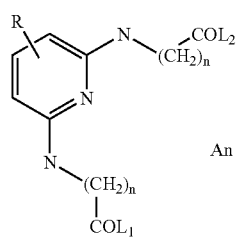

in which R may be H, $CF_3$, $CO_2Me$, $CO_2Et$, CN or $CONH_2$, R' represents a hydrogen atom, a $C_1$–$C_8$ alkyl radical optionally substituted with one or more hydroxyl, $C_1$–$C_2$ alkoxy, $C_2$–$C_4$ (poly)hydroxyalkoxy, amino, $C_1$–$C_2$ (di)alkylamine or optionally substituted aryl radicals, and R" represents a hydrogen atom, a $C_1$–$C_4$ alkyl radical optionally substituted with one or more hydroxyl, $C_1$–$C_2$ alkoxy, $C_2$–$C_4$ (poly)hydroxyalkoxy, amino, $C_1$–$C_2$ (di)alkylamino or optionally substituted aryl radicals, n is greater than 0, more particularly between 1 and 10 and preferably between 1 and 5; the electrical neutrality of the compounds being ensured by means of one or more cosmetically acceptable anions An.

Linkers that may be mentioned include the triazines described in WO 03/029359, the alkylenes mentioned in U.S. Pat. No. 5,708,151 and the Alkyl-aryl-Alkyls mentioned in U.S. Pat. No. 5,708,151.

It should be noted that any alkylene group in the main chain linking Dye 1/Dye 2, for the purposes of the present invention, is considered as being a linker.

An is an organic or mineral anion chosen, for example, from halides such as chlorides, bromides, fluorides or iodides; hydroxides, sulfates; hydrogen sulfates; ($C_1$–$C_6$) alkyl sulfates, for instance methyl sulfate or ethyl sulfate; phosphates; carbonates; hydrogen carbonates, perchlorates; acetates; tartrates; citrates; oxalates; ($C_1$–$C_6$)alkylsulfonates such as methanesulfonate; arylsulfonates optionally substituted with a $C_1$–$C_4$ alkyl radical, for instance a 4-tolylsulfonate.

By way of example, the mixed dye may be represented by the formula:

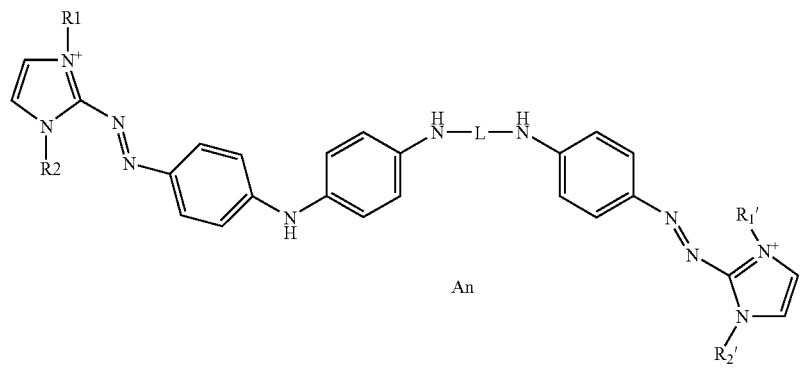

in which L is a linker as defined above, R1 and R1' are independently chosen from an alkyl radical, preferably of $C_1$–$C_6$, optionally substituted with one or more hydroxyl, $C_1$–$C_2$ alkoxy, $C_2$–$C_4$ (poly)hydroxyalkoxy, amino, $C_1$–$C_2$ (di)alkylamino or optionally substituted aryl radicals and R2 and R2' are independently chosen from a $C_1$–$C_6$ alkyl radical, optionally substituted with one or more hydroxyl, $C_1$–$C_2$ alkoxy, $C_2$–$C_4$ (poly)hydroxyalkoxy, amino or $C_1$–$C_2$ (di)alkylamino radicals; an optionally substituted phenyl radical; An represents one or more identical or different, monovalent or multivalent anions, as defined previously.

Examples of dyes corresponding to this formula that may be mentioned include:

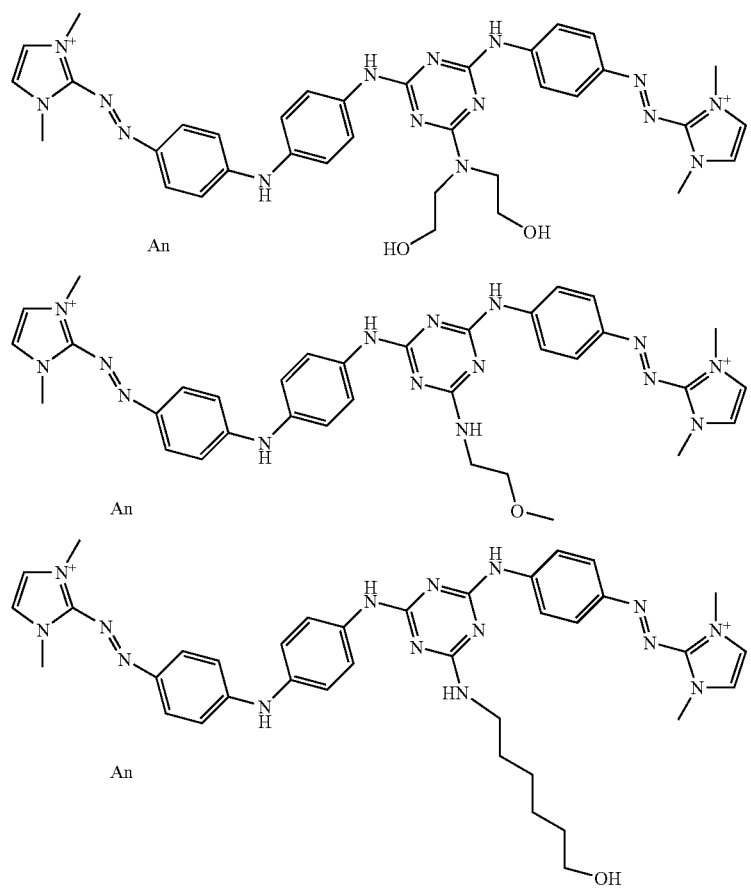

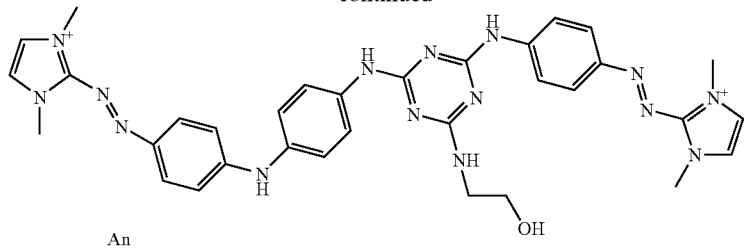

An

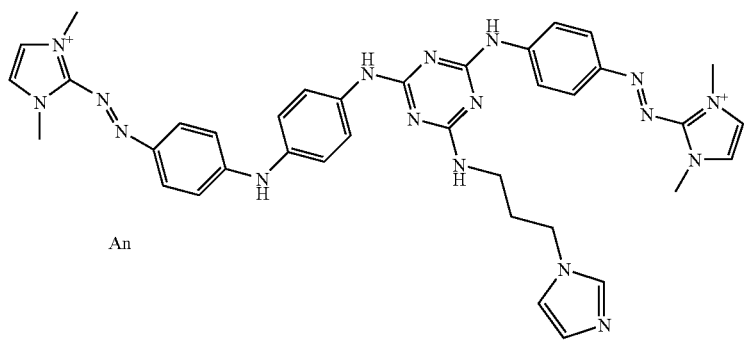

An

The composition of the present invention generally contains an amount of mixed dye of between 0.001% and 20% relative to the total weight of the composition. Preferably, this amount is between 0.005% and 10% and even more preferably between 0.01% and 5% relative to the total weight of the composition.

The dyes of the invention may be prepared according to chemical reactions that are known per se, starting with functionalized chromophores capable of reacting with the chosen linker. For example, when the linker is a triazine group, then the chromophore should comprise a reactive amino, OH or SH group and the synthesis may be performed according to the schemes below.

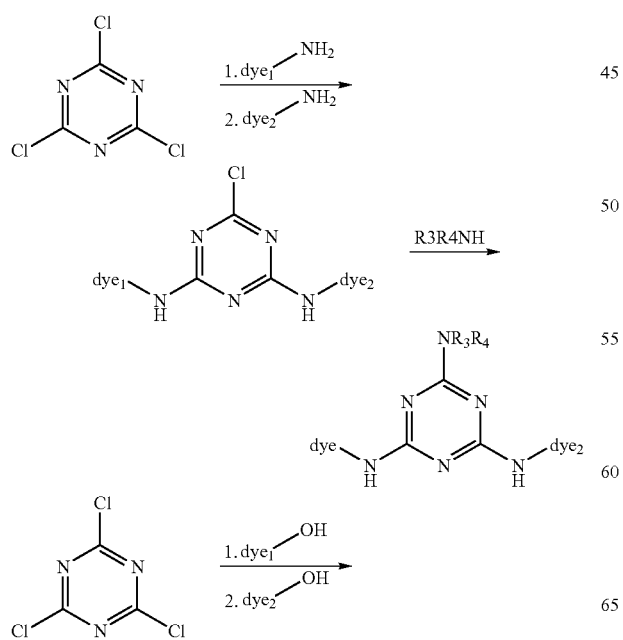

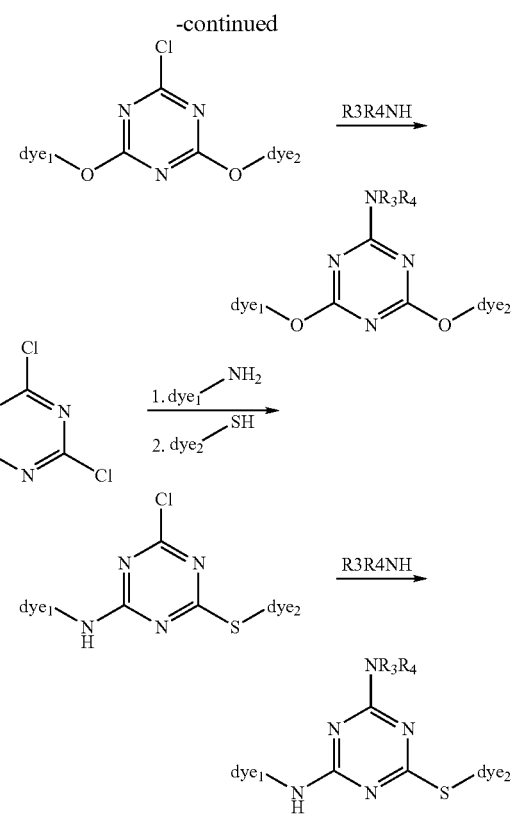

According to a first step, a first chromophore is mixed with the compound forming or capable of forming the linker, for example cyanuric chloride. When this reaction is complete, a second chromophore is added to the reaction medium. This sequence may be repeated as many times as there are reactive groups on the compound forming or capable of forming the linker.

For the preparation of a mixed dye Dye 1-L-Dye 2, the molar ratio of the linker relative to dye 1 is generally between 10:1 and 0.5:1 and preferably equal to 1:1. This ratio may be modified when more than one linker or several chromophores are used.

The reaction temperature is generally between −10° C. and +130° C. and preferably between −5° C. and 100° C. The reaction time depends on the reactivity of the species present and on the reaction temperature. In general, the reaction time is between 10 minutes and 8 hours and preferably between 30 minutes and 4 hours.

The pH of the reaction is generally between 3 and 10 and preferably between 4 and 8.

The reaction may be performed in water and/or in organic solvents, alone or as mixtures. Several publications describe the reaction for the chemical combination between two identical chromophores. Examples that may be mentioned include the documents ISBN 0901956759, WO 02/78596, DE 198 45 640, WO 03/029359 and U.S. Pat. No. 5,708,151.

In addition, the reactions or the reactions of a linker with two different compounds, which may or may not be dyes, have been described in the literature, for example in WO 03/029359, DE 3 335 956, WO 03/30909, WO 03/18021, Journal of Medicinal Chemistry 43(9), 2000,1892–97; Chemiker Zeitung 111(7–8), 1987, 241–5.

The dye composition in accordance with the invention may also contain one or more direct dyes conventionally used in the field of dyeing keratin fibers. In this respect, mention may be made especially of nitrobenzene dyes, azo direct dyes and methine direct dyes. These direct dyes may be of nonionic, anionic or cationic nature. Preferably, these additional direct dyes are of cationic nature.

The dye composition of the invention may contain one or more oxidation bases and/or one or more couplers conventionally used for dyeing keratin fibers.

Among the oxidation bases that may be mentioned are para-phenylenediamines, bis(phenyl)alkylenediamines, para-aminophenols, bis-para-aminophenols, ortho-aminophenols and heterocyclic bases, and the addition salts thereof.

Among these couplers that may especially be mentioned are meta-phenylenediamines, meta-aminophenols, meta-diphenols, naphthalene-based couplers and heterocyclic couplers, and the addition salts thereof.

In the composition of the present invention, the coupler(s) is (are) each generally present in an amount of between 0.001% and 10% and preferably between 0.005% and. 6% by weight approximately, relative to the total weight of the dye composition.

The oxidation base(s) present in the composition of the invention is (are) each generally present in an amount of between 0.001% and 10% and preferably between 0.005% and 6% by weight approximately, relative to the total weight of the dye composition.

In general, the addition salts of the oxidation bases and of the couplers that may be used in the context of the invention are especially chosen from the addition salts with an acid, such: as the hydrochlorides, hydrobromides, sulfates, alkyl sulfates, for instance methyl or ethyl sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The medium that is suitable for dyeing, also known as the dye support, is a cosmetic medium that generally consists of water or a mixture of water and at least one organic solvent to dissolve the compounds that would not be sufficiently soluble in water. As organic solvent, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The solvents are preferably present in proportions preferably of between 1% and 40% by weight approximately relative to the total weight of the dye composition, and even more preferably between 5% and 30% by weight approximately.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants are generally present in an amount for each of them of between 0.01% and 20% by weight relative to the weight of the composition.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The pH of the dye composition in accordance with the invention is generally between about 3 and 12 and preferably between about 5 and 11. It may be adjusted to the desired value using acidifying or basifying agents usually used in the dyeing of keratin fibers, or alternatively using standard buffer systems.

Among the acidifying agents that may be mentioned, for example, are inorganic or organic acids such as hydrochloric acid, orthophosphoric acid, sulfuric acid, carboxylic acids such as acetic acid, tartaric acid, citric acid and lactic acid, and sulfonic acids.

Among the basifying agents that may be mentioned, for example, are aqueous ammonia, alkaline carbonates, alkanolamines such as mono-, di- and triethanolamine and derivatives thereof, sodium hydroxide, potassium hydroxide and the compounds of formula (II) below:

(II)

in which W is a propylene residue that is unsubstituted or substituted with a hydroxyl group or a $C_1$–$C_4$ alkyl radical; $R_a$, $R_b$, $R_c$ and $R_d$, which may be identical or different, represent a hydrogen atom, a $C_1$–$C_4$ alkyl radical or a $C_1$–$C_4$ hydroxyalkyl radical.

The dye composition according to the invention may be in various forms, such as in the form of liquids, creams or gels, or in any other form that is suitable for dyeing keratin fibers, and especially human hair.

The process of the present invention is a process in which the composition according to the present invention as defined above is applied to the fibers. According to one particular embodiment, the composition of the invention is applied to the keratin fibers in the presence of an oxidizing agent, for a time that is sufficient to obtain the desired lightening. The oxidizing agent may be added to the composition of the invention just at the time of use, or it may be implemented starting with an oxidizing composition containing it, applied simultaneously or sequentially to the composition of the invention.

According to one particular embodiment, the composition according to the present invention is mixed, preferably at the time of use, with a composition containing, in a medium that is suitable for dyeing, at least one oxidizing agent, this oxidizing agent being present in an amount that is sufficient to obtain the desired lightening. The mixture obtained is then applied to the keratin fibers. After an action time of 3 to 50 minutes approximately, preferably 5 to 30 minutes approximately, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibers ranges preferably between 3 and 12 approximately and even more preferably between 5 and 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels or any other form that is suitable for dyeing keratin fibers, and especially human hair.

Another subject of the invention is a multi-compartment dyeing device or "kit", in which a first compartment contains the above-defined dye composition of the present invention and a second compartment contains an oxidizing agent. This device may be equipped with a means for applying the desired mixture to the hair, such as the devices described in patent FR-2 586 913 in the name of the Applicant.

The examples below illustrate the invention without, however, limiting its scope.

EXAMPLES

Examples of Synthesis

Step 1:

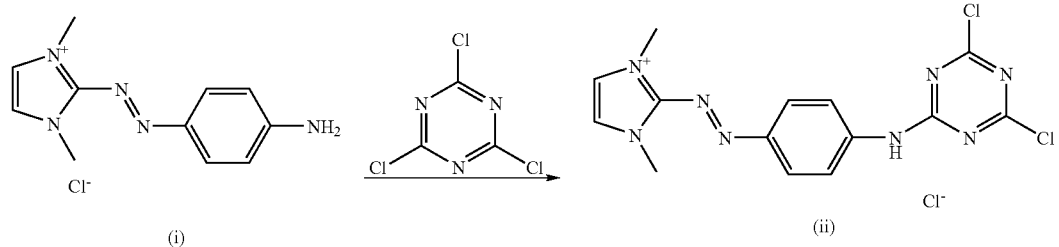

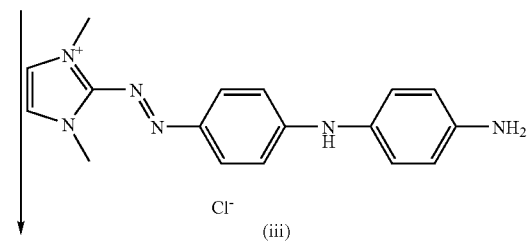

-continued

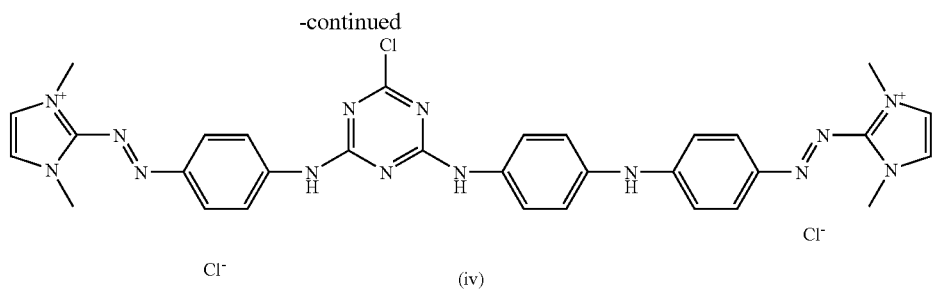

2.4 g of cyanuric chloride in 50 ml of acetone are added at room temperature and with stirring into a 500 ml three-necked flask. The reaction medium is transparent. A mixture consisting of water and ice in a respective proportion of 50 ml and 100 ml is added, and the reaction medium is placed

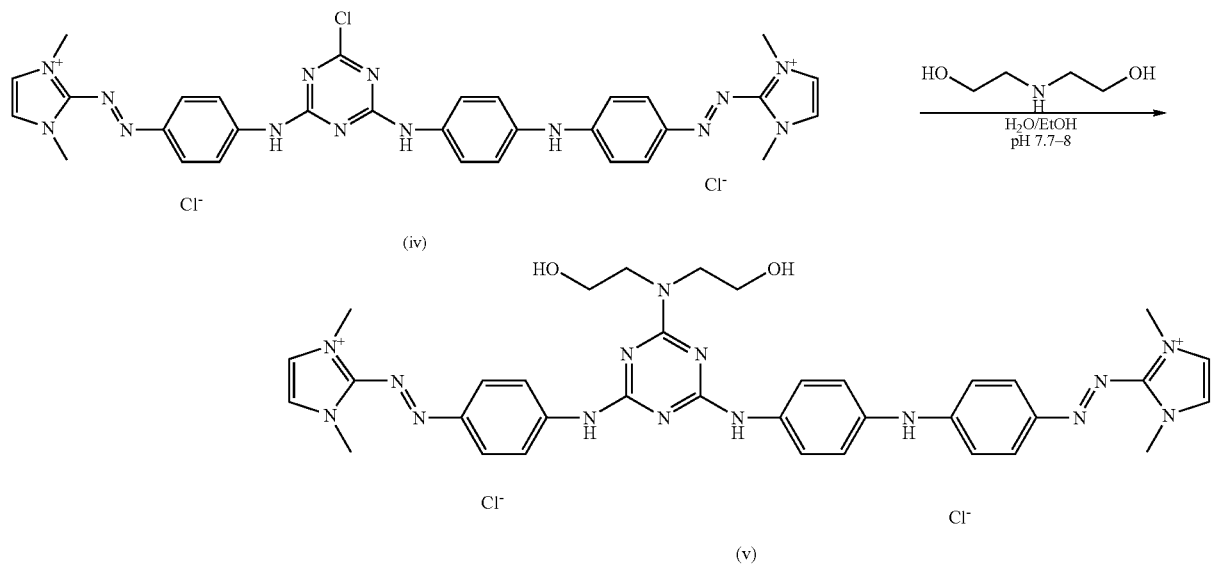

at 0° C. in an ice bath. After stirring for a few seconds, a whitish suspension is obtained. The pH value is 2.8. Using a dropping funnel, a solution containing 3.2 g of (i) dissolved in 100 ml of water is added, taking care to maintain the pH of the reaction medium at between 4 and 6 by means of saturated $K_2CO_3$ solution, and to keep the reaction medium at a temperature below 5° C.

After this addition, the pH is stabilized to 4.8 by uniform addition of saturated $K_2CO_3$ solution. The mixture is then allowed to return to room temperature. HPLC (relative purity: 94%) and a control mass (m/z: 363–365–367) indicate the virtually exclusive formation of the reaction product (ii).

A solution consisting of 3.42 g of (iii) predissolved in 50 ml of an $H_2O$/EtOH mixture (1/1) is then added to the above reaction medium, taking care to maintain the pH between 4 and 6. After addition, the pH is maintained at 4.9–5 for 15 minutes. The reaction medium is then heated at 44° C. for 2.5 hours. The reaction medium is allowed to return to room temperature and is then poured into a conical flask containing 1 liter of a solution consisting of isopropanol and acetone. A precipitate appears. This precipitate is filtered off, dried in a desiccator and then analyzed. 6.08 g (yield=86%) of a brown powder (product (iv)) are obtained in a purity equal to 98% (relative purity, HPLC).

Step 2:

9 g of (iv) dissolved in 300 ml of water are placed in a three-necked flask on which is mounted a condenser, a pH probe and an addition funnel containing 1N sodium hydroxide solution. The reaction medium is then heated to 85° C. (oil bath temperature: 96° C.) and the pH is adjusted to between 7.7 and 8 using the sodium hydroxide solution. The amine (3 ml) diluted in 20 ml of water is then added very slowly, taking care to monitor the pH (pH<8). As soon as the addition is complete, the reaction medium is brought to 92° C. (oil bath temperature: 118° C.) and is stirred until the pH stabilizes at a value of between 7.7 and 8.

After reaction for one hour, the reaction medium is cooled and then poured into a conical flask containing 1 liter of acetone. The product precipitates out. It is then filtered off, dried in a desiccator and then analyzed. 7.1 g of a brown powder (compound v) are obtained (yield=82%, HPLC purity: 92%).

Mass (ESI+): m/z=352

NMR ($^1$H, 400 MHz, MeOD): 3.86–3.87 ppm (broad s, 4H), 4.05 ppm (s, 6H), 4.12 ppm (s, 6H), 4.88 ppm (broad s, 4H), 7.10–7.12 ppm (d, 2H), 7.28–7.26 ppm (d, 2H), 7.55 ppm (s, 2H), 7.69 ppm (s, 2H), 7.77–7.79 ppm (d, 2H), 7.97–7.95 ppm (d, 2H), 8.09–8.04 ppm (m, 4H).

The following compounds were synthesized by performing step 2 using the reagents indicated below.

| Structure of R | Reagent used | Mass (ESI +) m/z | HPLC purity (%) | Yield (%) |
|---|---|---|---|---|
| ~NH* (propyl) | ~NH₂ (propyl) | 329 | 95 | 48 |
| methoxyethyl-NH* | methoxyethyl-NH₂ | 337 | 97 | 73 |
| HO-(CH₂)₆-N(CH₃)* | HO-(CH₂)₆-NHCH₃ | 358 | 97 | 61 |
| imidazolyl-propyl-*NH | imidazolyl-propyl-NH₂ | 362 | 97 | 82 |
| HO-CH₂CH₂-*NH | HO-CH₂CH₂-NH₂ | 330 | 98 | 94 |
| *N-methylpiperazinyl | N-methylpiperazine (NH) | 349 | 98 | 71 |
| *N-morpholinyl | morpholine (NH) | 342 | 95 | 56 |
| long alkyl-NH* | long alkyl-NH₂ | 371 | 74 | 66 |

Examples of Dyeing

Invention Examples

The following dye compositions were prepared:

| | |
|---|---|
| (50/50 C8/C10) alkyl polyglucoside as a buffered aqueous 60% solution, sold under the name Oramix-CG110 by the company SEPPIC | 10 g |
| Benzyl alcohol | 10 g |
| Polyethylene glycol 400 containing 8 ethylene oxide units | 12 g |
| Cationic mixed dye (I) | $4.7 \times 10^{-4}$ mol. |
| 20.5% aqueous ammonia | 13 g |
| Demineralized water | qs 100 g |

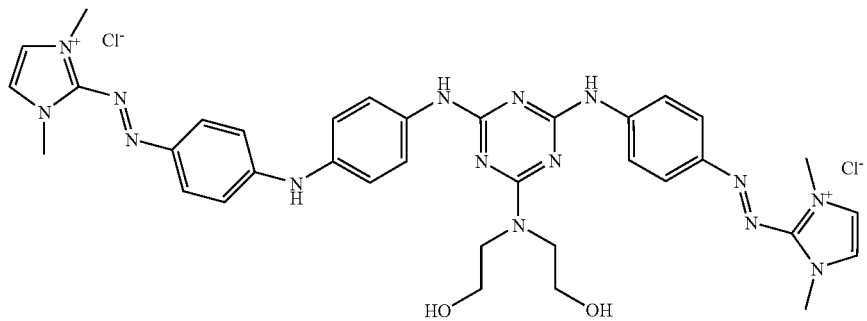

(I)

At the time of use, the above composition is mixed with 40 V (weight for weight) aqueous hydrogen peroxide solution. The mixture is then applied to locks of natural gray (NG) or permanent-waved gray (PG) hair containing 90% white hairs. The leave-in time on the locks is 20 minutes at room temperature. The locks are then shampooed.

After drying, the color uptake is evaluated visually and by measuring the L*a*b* (CM 2002 colorimeter, illuminant D65-10° CSI).

The selectivity is evaluated by means of the difference between the level of coloration of a natural lock (NG) and a permanent-waved lock (PG) from the L*a*b* values measured for each type of lock, according to the following formula:

$$\Delta E_{ng/pg} = \sqrt{(L_{pg}^* - L_{ng}^*)^2 + (a_{pg}^* - a_{ng}^*)^2 + (b_{pg}^* - b_{ng}^*)^2}$$

The chromaticity C* is calculated from the following formula, in which $$C^* = \sqrt{(a^*)^2 + (b^*)^2}$$

The results are collated in table 1 below.

The colored locks are then shampooed 12 times, with intermediate drying between two shampoo washes. The color after the 12 shampoo washes is compared with the initial color of the dyed lock, visually and by calorimetric measurement. The shampoo fastness is measured on dyed natural hair and on dyed permanent-waved hair according to the formula for ΔE above, using the L*a*b* values measured on each type of lock before and after the 12 shampoo washes.

The colorimetric measurements are collated in table 1 below.

TABLE 1

| | L* | a* | b* | C* | Shampoo fastness |
|---|---|---|---|---|---|
| Dyed natural (NG) hair | 27.7 | 5.6 | −0.9 | 5.6 | — |
| Dyed permanent-waved (PG) hair | 24.15 | 4.9 | −0.5 | 4.9 | — |
| Dyed natural (NG) hair after 12 shampoo washes | 28.2 | 5.5 | −1.65 | 5.7 | 0.9 |
| Dyed permanent-waved (PG) hair after 12 shampoo washes | 22.2 | 4.3 | −1.8 | 4.7 | 2.1 |

The results indicated in table 1 show that the color obtained is strong and sparingly chromatic (violet-black). They moreover show good shampoo fastness, both on natural hair and on permanent-waved hair. In addition, no changing of color is observed.

Comparative Examples

The following dye composition was prepared;

| | |
|---|---|
| (50/50 C8/C10)alkyl polyglucoside as a buffered aqueous 60% solution | 10 g |
| Benzyl alcohol | 10 g |
| Polyethylene glycol 400 containing 8 ethylene oxide units | 12 g |
| Violet dye (II) | 4.7 × 10⁻⁴ mol. |
| Orange dye (III) | 4.7 × 10⁻⁴ mol. |
| 20.5% aqueous ammonia | 13 g |
| Demineralized water | qs 100 g |

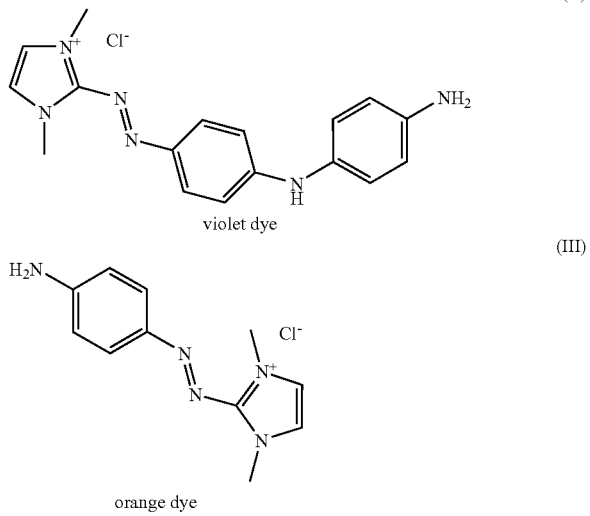

The orange dye is sold under the name Basic Orange 31. The violet dye is synthesized according to the method described in U.S. Pat. No. 5,708,151.

At the time of use, the composition is mixed with 40 V (weight for weight) aqueous hydrogen peroxide solution. The mixture is then applied to a lock of natural gray (NG) or permanent-waved gray (PG) hair containing 90% white hairs. The leave-in time on the locks is 20 minutes at room temperature. The locks are then shampooed.

After drying, the color uptake is evaluated visually and by L*a*b* colorimetric measurement as defined above (CM 2002 calorimeter, illuminant D65-10° CSI).

The dyed locks are then shampooed 12 times, with intermediate drying between two shampoo washes. The color after the 12 shampoo washes is compared with the initial color of the dyed lock, visually and by colorimetric measurement.

The selectivity and the shampoo fastness are determined according to the method described previously. The results are collated in table 2 below.

TABLE 2

| | L* | a* | b* | C* | Shampoo fastness |
|---|---|---|---|---|---|
| Dyed natural (NG) hair | 19.4 | 6.4 | −0.4 | 6.4 | |
| Dyed permanent-waved (PG) hair | 17.4 | 1.85 | −0.15 | 1.9 | |
| Dyed natural (NG) hair after 12 shampoo washes | 20.6 | 9.0 | −3.2 | 9.6 | 4.1 |
| Dyed permanent-waved (PG) hair after 12 shampoo washes | 18.7 | 8.0 | −7.3 | 10.85 | 9.5 |

The results of the coloration derived from the mixture of violet and orange dyes show that although the color obtained is sparingly chromatic, it varies as a function of the nature of the hair that is dyed. Specifically, by comparing the values of a*, the color obtained on the natural hair is red, whereas on permanent-waved hair it is black. Furthermore, a change of color toward violet is observed both on natural hair and on permanent-waved hair.

Comparison of the results of table 1 and of table 2 shows that the present invention makes it possible to obtain uniform colorations irrespective of the nature of the dyed hair, without changing of color, and which show good shampoo fastness.

The invention claimed is:

1. A dye composition comprising, in a suitable dyeing medium, at least one mixed direct dye, said mixed direct dye comprising at least two different chromophores linked together via a linker, the chromophores being chosen such that the at least one mixed direct dye, when present in the composition in an amount of $4.7 \times 10^{-4}$ mol of dye per 100 g of composition, gives, in a standardized coloration test on a lock of hair comprising 90% white hairs, the following values in the L*a*b* colorimetric system:

if $a^* \geq 0$ and $b^* \geq 0$, then a* ranges from 0 to 20, and b* ranges from 0 to 40;

if $a^* \leq 0$ and $b^* \geq 0$, then a* ranges from −27 to 0, and b* ranges from 0 to 40;

if $a^* \geq 0$ and $b^* \leq 0$, then a* ranges from 0 to +9, and b* ranges from −10 to 0;

if $a^* \leq 0$ and $b^* \leq 0$, then a* ranges from −14 to 0, and b* ranges from −21 to 0.

2. The composition according to claim 1, wherein the values a* and b* are such that:

if $a^* \geq 0$ and $b^* \geq 0$, then a* ranges from 0 to 15, and b* ranges from 0 to 30;

if $a^* \leq 0$ and $b^* \geq 0$, then a* ranges from −20 to 0, and b* ranges from 0 to 30;

if $a^* \geq 0$ and $b^* \leq 0$, then a* ranges from 0 to 6, and b* ranges from −6 to 0;

if $a^* \leq 0$ and $b^* \leq 0$, then a* ranges from −10 to 0, and b* ranges from −15 to 0.

3. The composition according to claim 1, wherein the at least one mixed direct dye has a chromaticity that is less than or equal to 20.

4. The composition according to claim 1, wherein the at least two different chromophores are chosen from acridines, acridones, anthranthrones, anthrapyrimidines, anthraquinones, azines, azos, azomethines, benzanthrones, benzimidazoles, benzimidazolones, benzindoles, benzoxazoles, benzopyrans, benzothiazoles, benzoquinones, bis-azines, bis-isoindolines, carboxanilides, coumarins, cyanins, diazines, diketopyrrolopyrroles, dioxazines, diphenylamines, diphenylmethanes, dithiazines, flavonoids, fluorindines, formazans, hydrazones, hydroxy ketones, indamines, indanthrones, indigoids, pseudo-indigoids, indophenols, indoanilines, isoindolines, isoindolines, isoindolinones, isovianlanthrones, lactones, methines, naphthalimides, naphthanilides, naphtholactams, naphthoquinones, nitro dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, and xanthenes.

5. The composition according to claim 4, wherein the at least two different chromophores are chosen from acridine, acridone, anthranthrone, anthraquinone, azine, azo, azomethine, benzanthrone, benzoquinone, bis-azine, cyanin, diazine, diketopyrrolopyrrole, dioxazine, diphenylmethane, dithiazine, flavonoids, formazans, hydrazones, indamines, indanthrones, indigoids, pseudo-indigoids, indophenols, indoanilines, isoviolanthrones, methines, naphthalimides, naphtholactams, naphthoquinones, nitro dyes, phenazines, phenothiazines, phthalocyanin, polyenes/carotenoids, porphyrins, pyrazolones, quinacridones, quinophthalones, stilbenes, tetrazoliums, thiazines, thioindigo, thiopyronines, triarylmethanes, and xanthenes.

6. The composition according to claim 5, wherein the at least two different chromophores are chosen from azo, xanthene, hydrazone, arylhydrazone, phenothiazine, acridine, diketopyrrolopyrrole, cyanin, anthraquinone, methine, azomethine, indigoid and nitro chromophores.

7. The composition according to claim 1, wherein the at least one mixed direct dye comprises at least one chromophore which, by itself, has a positive or zero value of a* and b*, and at least one chromophore which, by itself, has a negative value of a* and b*.

8. The composition according to claim 1, wherein the at least one mixed direct dye comprises at least one chromophore which, by itself, has a positive or zero value of a* and a negative or zero value of b*, and at least one chromophore which, by itself, has a negative value of a* and a positive value of b*.

9. The composition according to claim 1, wherein the at least one mixed direct dye comprises at least one chromophore which, by itself, has a positive or zero value of a* and b* and at least one chromophore which, by itself, has a positive or zero value of a* and a negative value of b*.

10. The composition according to claim 1, wherein the at least one mixed direct dye comprises at least one chromophore which, by itself, has a positive or zero value of a* and b* and at least one chromophore which, by itself, has a negative value of a* and a positive value of b*.

11. The composition according to claim 1, wherein the at least one mixed dye comprises at least one chromophore which, by itself, has a positive or zero value of a* and a negative or zero value of b*, and at least one chromophore which, by itself, has a negative value of a* and b*.

12. The composition according to claim 1, wherein the at least one mixed direct dye comprises at least one chromophore which, by itself, has a negative or zero value of a* and b* and at least one chromophore which, by itself, has a negative value of a* and a positive value of b*.

13. The composition according to claim 1, wherein the at least one mixed direct dye comprises an amount of different chromophores ranging from two to four.

14. The composition according to claim 13, wherein the at least one mixed direct dye comprises an amount of different chromophores ranging from two to three.

15. The composition according to claim 1, wherein the at least one mixed direct dye is chosen from those of formula: Dye 1-L-Dye 2, wherein L is a cationic or non-cationic linker and Dye 1 and Dye 2 are different chromophores.

16. The composition according to claim 1, wherein the at least one mixed direct dye is cationic.

17. The composition according to claim 1, wherein the at least one mixed direct dye comprises two or three different chromophores, wherein at least two of the chromophores are cationic.

18. The composition according to claim 16, wherein at least one of the at least two cationic chromophores is a chromophore comprising a quaternized nitrogen atom.

19. The composition according to claim 1, wherein the at least one mixed direct dye comprises at least two cationic azo chromophores.

20. The composition according to claim 1, wherein the linker is chosen from a $C_1$–$C_{20}$ linear, branched or cyclic, optionally substituted hydrocarbon-based chain, wherein at feast one of the carbon atoms of the chain may be replaced with at least one hetero atom, and/or with at least one group comprising a hetero atom, further wherein the hydrocarbon-based chain may be unsaturated or may comprise at least one radical chosen from optionally substituted alkylene radicals, optionally substituted arylene radicals, optionally substituted divalent terephthalamide radicals, optionally substituted divalent heterocyclic radicals, and —NH—CO— radicals.

21. The composition according to claim 1, wherein the linker is chosen from a $C_1$–$C_{14}$ linear, branched or cyclic, optionally substituted hydrocarbon-based chain, wherein at least one of the carbon atoms of the chain may be replaced with at least one hetero atom, and/or with at least one group comprising a hetero atom, further wherein the hydrocarbon-based chain may be unsaturated or may comprise at least one radical chosen from optionally substituted alkylene radicals, optionally substituted arylene radicals, optionally substituted divalent terephthalamide radicals, optionally substituted divalent heterocyclic radicals, and —NH—CO— radicals.

22. The composition according to claim 1, wherein the linker comprises an atom or a group of atoms separating the at least two different chromophores of the at least one mixed direct dye, which are such that the position on the scale of wavelengths of the absorption maximas of the at least two different chromophores are not modified by more than 30 nm relative to the absorption maxima of each of the two different chromophores taken separately.

23. The composition according to claim 1, wherein the at least one mixed direct dye is chosen from those of formula:

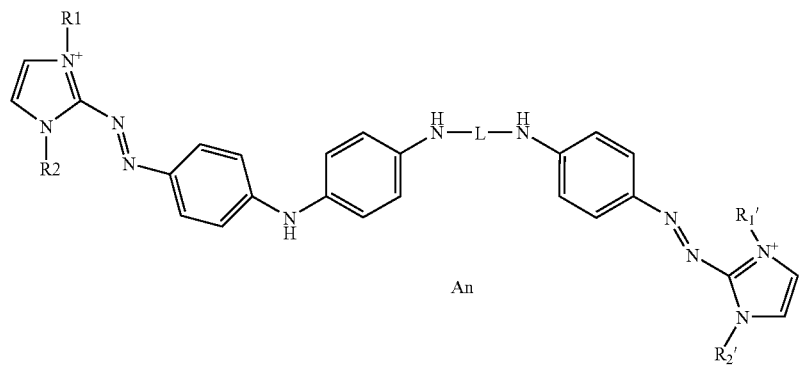

wherein
L is a linker,
R1 and R1', which may be identical or different, are chosen from $C_1$–$C_6$ alkyl radicals, optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino and optionally substituted aryl radicals,
R2 and R2', which may be identical or different, are chosen from $C_1$–$C_6$ alkyl radicals, optionally substituted with at least one radical chosen from hydroxyl, $C_1$–$C_2$ alkoxy, $C_2$–$C_4$ (poly)hydroxyalkoxy, amino and $C_1$–$C_2$ (di)alkylamino radicals; and optionally substituted phenyl radicals; and
An is at least one, identical or different, monovalent or multivalent anion.

24. The composition according to claim 23, wherein the at least one mixed direct dye is chosen from the following structures:

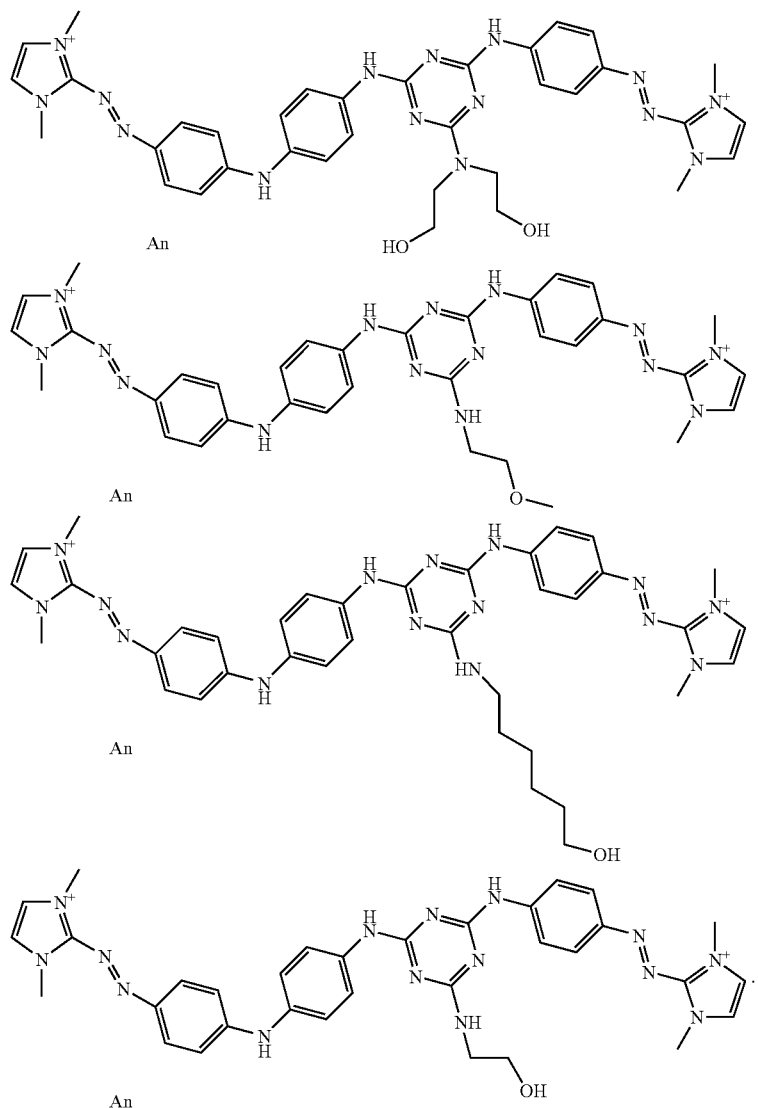

25. The composition according to claim 23, wherein the at least one anion An is chosen from organic and mineral anions.

26. The composition according to claim 25, wherein the at least one anion An is chosen from halides, hydroxides, sulfates, hydrogen sulfates, ($C_1$–$C_6$)alkyl sulfates, phosphates, carbonates, hydrogen carbonates, perchlorates, acetates, tartrates, citrates, oxalates, ($C_1$–$C_6$)alkylsulfonates, and arylsulfonates optionally substituted with at least one $C_1$–$C_4$ alkyl radical.

27. The composition according to claim 1, wherein the at least one mixed direct dye is present in an amount ranging from 0.001% to 20% by weight, relative to the total weight of the composition.

28. The composition according to claim 27, wherein the at least one mixed direct dye is present in an amount ranging from 0.01% to 5% by weight, relative to the total weight of the composition.

29. The composition according to claim 1, further comprising at least one direct dye other than the at least one mixed direct dye.

30. The composition according to claim 1, further comprising at least one oxidation base chosen from para-phenylenediamines, bis(phenyl)alkylenediamines, para-aminophenols, ortho-aminophenols, heterocyclic bases, and the addition salts thereof.

31. The composition according to claim 1, further comprising at least one coupler chosen from meta-phenylenediamines, meta-aminophenols, meta-diphenols, naphthalene-based couplers, heterocyclic couplers, and the addition salts thereof.

32. The composition according to claim 30, wherein the at least one oxidation base is present in an amount ranging from 0.001% to 10% by weight, relative to the total weight of the dye composition.

33. The composition according to claim 31, wherein the at least one coupler is present in an amount ranging from 0.001% to 10% by weight, relative to the total weight of the dye composition.

34. The composition according to claim 1, wherein the pH ranges from 3 to 12.

35. The composition according to claim 34, wherein the pH ranges from 5 to 11.

36. The composition according to claim 1, further comprising at least one alkaline agent.

37. The composition according to claim 1, further comprising at least one oxidizing agent.

38. A process for the dyeing of keratin fibers, comprising applying to the keratin fibers a dye composition comprising, in a suitable dyeing medium, at least one mixed direct dye, said mixed direct dye comprising at least two different chromophores linked together via a linker, the chromophores being chosen such that the at least one mixed direct dye, when present in the composition in an amount of $4.7 \times 10^{-4}$ mol of dye per 100 g of composition, provides, in a standardized coloration test on a lock of hair comprising 90% white hairs, the following values in the L*a*b* colorimetric system:

if $a^* \geq 0$ and $b^* \geq 0$, then a* ranges from 0 to 20, and b* ranges from 0 to 40;

if $a^* \leq 0$ and $b^* \geq 0$, then a* ranges from −27 to 0, and b* ranges from 0 to 40;

if $a^* \geq 0$ and $b^* \leq 0$, then a* ranges from 0 to 9, and b* ranges from −10 to 0;

if $a^* \leq 0$ and $b^* \leq 0$, then a* ranges from −14 to 0, and b* ranges from −21 to 0;

and wherein the dye composition is left on the fibers for a period of time that is sufficient to develop the desired coloration.

39. The process according to claim 38, wherein the dye composition is applied to the fibers in the presence of at least one oxidizing agent.

40. The process according to claim 39, wherein the at least one oxidizing agent is chosen from hydrogen peroxide, urea peroxide, alkali metal bromates, persalts, peracids and oxidase enzymes.

41. A multi-compartment kit comprising:

at least one first compartment comprising a dye composition comprising, in a suitable dyeing medium, at least one mixed direct dye, said mixed direct dye comprising at least two different chromophores linked together via a linker, the chromophores being chosen such that the at least one mixed direct dye, when present in the composition in an amount of $4.7 \times 10^{-4}$ mol of dye per 100 g of composition, provides, in a standardized coloration test on a lock of hair comprising 90% white hairs, the following values in the L*a*b* colorimetric system:

if $a^* \geq 0$ and $b^* \geq 0$, then a* ranges from 0 to 20, and b* ranges from 0 to 40;

if $a^* \leq 0$ and $b^* \geq 0$, then a* ranges from −27 to 0, and b* ranges from 0 to 40;

if $a^* \geq 0$ and $b^* \leq 0$, then a* ranges from 0 to 9, and b* ranges from −10 to 0;

if $a^* \leq 0$ and $b^* \leq 0$, then a* ranges from −14 to 0, and b* ranges from −21 to 0; and at least one second compartment comprising at least one oxidizing agent.

42. A method of obtaining good shampoo fastness for dyed keratin fibers, comprising applying to the keratin fibers a composition comprising, in a suitable dyeing medium, at least one mixed direct dye, said mixed direct dye comprising at least two different chromophores linked together via a linker, the chromophores being chosen such that the at least one mixed direct dye, when present in the composition in an amount of $4.7 \times 104$ mol of dye per 100 g of composition, gives, in a standardized coloration test on a lock of hair comprising 90% white hairs, the following values in the L*a*b* colorimetric system:

if $a^* \geq 0$ and $b^* \geq 0$, then a* ranges from 0 to 20, and b* ranges from 0 to 40;

if $a^* \leq 0$ and $b^* \geq 0$, then a* ranges from −27 to 0, and b* ranges from 0 to 40;

if $a^* \geq 0$ and $b^* \leq 0$, then a* ranges from 0 to 9, and b* ranges from −10 to 0;

if $a^* \leq 0$ and $b^* \leq 0$, then a* ranges from −14 to 0, and b* ranges from −21 to 0;

and wherein the dyeing composition is allowed to remain in contact with the keratin fibers for a period of time sufficient to obtain the desired coloration.

43. A mixed direct dye comprising at least two different chromophores linked together via a linker, the chromophores being chosen such that the at least one mixed direct dye, when present in a composition in an amount of $4.7 \times 10^{-4}$ mol of dye per 100 g of composition, provides, in a standardized coloration test on a lock of hair comprising 90% white hairs, the following values in the L*a*b* colorimetric system:

if $a^* \geq 0$ and $b^* \geq 0$, then a* ranges from 0 to 20, and b* ranges from 0 to 40;

if $a^* \leq 0$ and $b^* \geq 0$, then a* ranges from −27 to 0, and b* ranges from 0 to 40;

if $a^* \geq 0$ and $b^* \leq 0$, then a* ranges from 0 to 9, and b* ranges from −10 to 0;

if $a^* \leq 0$ and $b^* \leq 0$, then a* ranges from −14 to 0, and b* ranges from −21 to 0.

44. A process for preparing the at least one mixed direct dye according to claim 43, comprising reacting a first chromophore with a compound that can form the linker, and, when the first chromophore reaction is complete, adding a second chromophore to the reaction medium; this sequence possibly being repeated as many times as there are reactive groups on the compound that can form the linker.

* * * * *

UNITED STATES PATENT AND TRADEMARK OFFICE
CERTIFICATE OF CORRECTION

PATENT NO. : 7,201,779 B2 Page 1 of 1
APPLICATION NO. : 10/980900
DATED : April 10, 2007
INVENTOR(S) : Henri Samain et al.

It is certified that error appears in the above-identified patent and that said Letters Patent is hereby corrected as shown below:

- In claim 20, at column 27, line 63, "feast" should read -- least --

- In claim 20, at column 28, lines 2-3, "-NH-CO-radicals." should read
-- -NH-CO-radicals. --.

- In claim 21, at column 28, lines 14-15, "-NH-CO-radicals." should read
-- -NH-CO-radicals. --.

- In claim 42, at column 32, line 13, "of4.7x104" should read -- of $4.7 \times 10^{-4}$ --.

Signed and Sealed this

Twenty-ninth Day of May, 2007

JON W. DUDAS
*Director of the United States Patent and Trademark Office*